(12) United States Patent
Chen et al.

(10) Patent No.: US 8,664,952 B2
(45) Date of Patent: Mar. 4, 2014

(54) SIMULTANEOUS DIFFUSION IMAGING OF MULTIPLE CROSS SECTIONS

(75) Inventors: Jyh-Horng Chen, Taipei (TW); Tzi-Dar Chiueh, Taipei (TW); Edzer L. Wu, Taipei (TW)

(73) Assignee: National Taiwan University, Taipei (TW)

( * ) Notice: Subject to any disclaimer, the term of this patent is extended or adjusted under 35 U.S.C. 154(b) by 485 days.

(21) Appl. No.: 13/088,557

(22) Filed: Apr. 18, 2011

(65) Prior Publication Data

US 2011/0254550 A1 Oct. 20, 2011

Related U.S. Application Data

(63) Continuation-in-part of application No. 12/370,214, filed on Feb. 12, 2009, now Pat. No. 8,049,496, which is a continuation-in-part of application No. 12/337,388, filed on Dec. 17, 2008, now Pat. No. 8,022,701.

(60) Provisional application No. 61/325,657, filed on Apr. 19, 2010.

(51) Int. Cl.
 *G01V 3/00* (2006.01)
(52) U.S. Cl.
 USPC .......................................... 324/307; 324/309

(58) Field of Classification Search
 USPC .................. 324/307, 309, 306, 312, 314, 300
 See application file for complete search history.

(56) References Cited

U.S. PATENT DOCUMENTS

| | | | | |
|---|---|---|---|---|
| 6,614,225 | B1* | 9/2003 | Feinberg | 324/307 |
| 8,049,496 | B2* | 11/2011 | Chen et al. | 324/307 |
| 2012/0056620 | A1* | 3/2012 | Feinberg et al. | 324/309 |
| 2013/0181710 | A1* | 7/2013 | Setsompop et al. | 324/309 |

* cited by examiner

*Primary Examiner* — Louis Arana
(74) *Attorney, Agent, or Firm* — Occhiuti & Rohlicek LLP

(57) ABSTRACT

A diffusion imaging method is provided. The diffusion imaging method includes performing a plurality of data collection sequences. Each data collection sequence includes applying an excitation radio frequency signal and a selection gradient. The excitation radio frequency signal includes a first set of frequency bands selected to simultaneously excite a first nuclei type in a plurality of cross sections of a subject. Each data collection sequence further includes applying a diffusion gradient during formation of a magnetic resonance signal, applying a spatial encoding gradient during formation of the magnetic resonance signal, and while acquiring the magnetic resonance signal, applying a separation gradient to change a frequency separation between portions of the magnetic resonance signal. The diffusion imaging method further includes computationally determining a diffusion image of each of the plurality of cross sections.

8 Claims, 19 Drawing Sheets

| Nucleus | Gyromagnetic Ratio (MHz/T) |
|---|---|
| $^1$H | 42.58 |
| $^2$H | 6.54 |
| $^3$He | 32.44 |
| $^{13}$C | 10.71 |
| $^{14}$N | 3.08 |
| $^{17}$O | 5.77 |
| $^{19}$F | 40.08 |
| $^{23}$Na | 11.27 |
| $^{31}$P | 17.25 |
| $^{129}$Xe | 11.86 |

FIG. 1

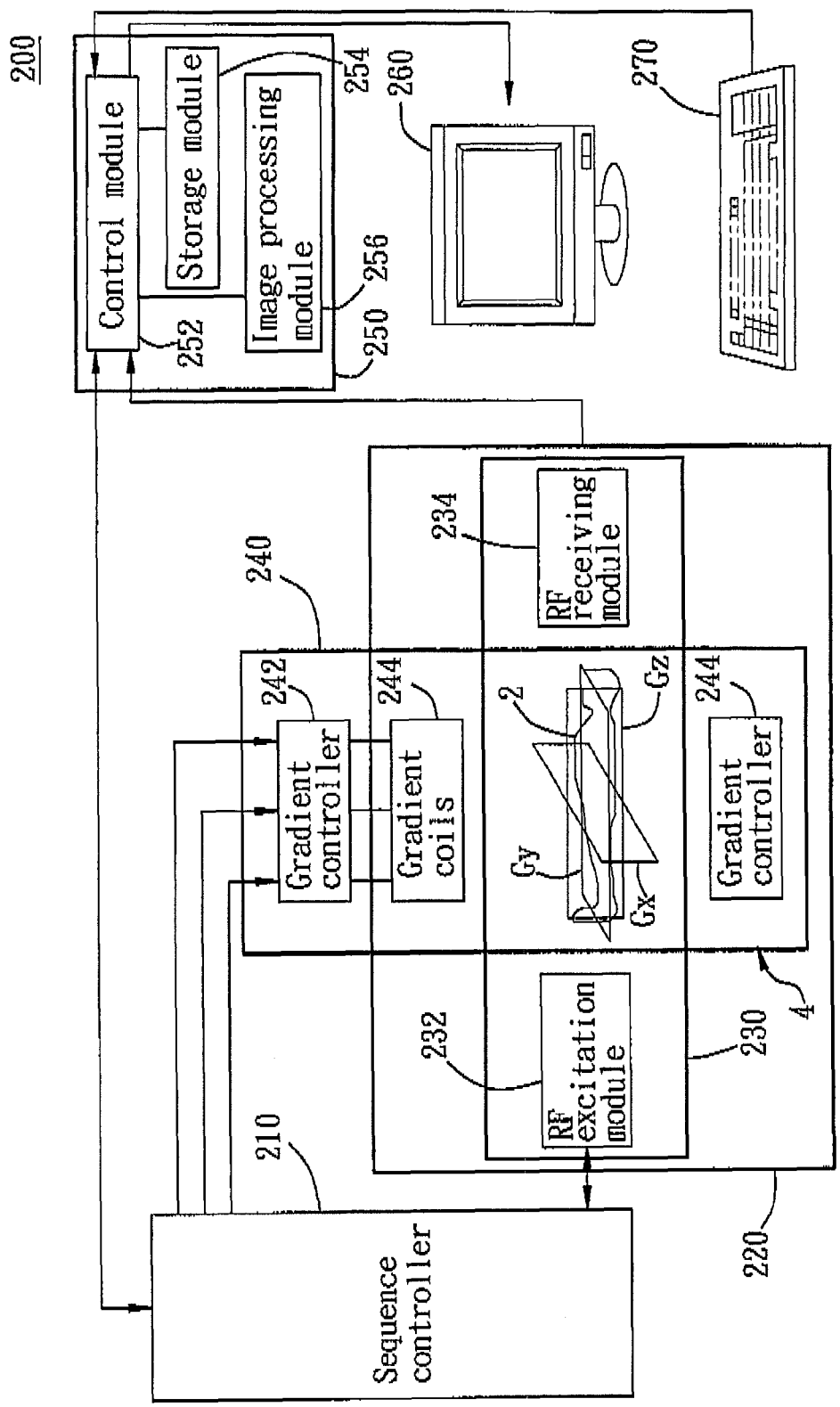
F I G. 2

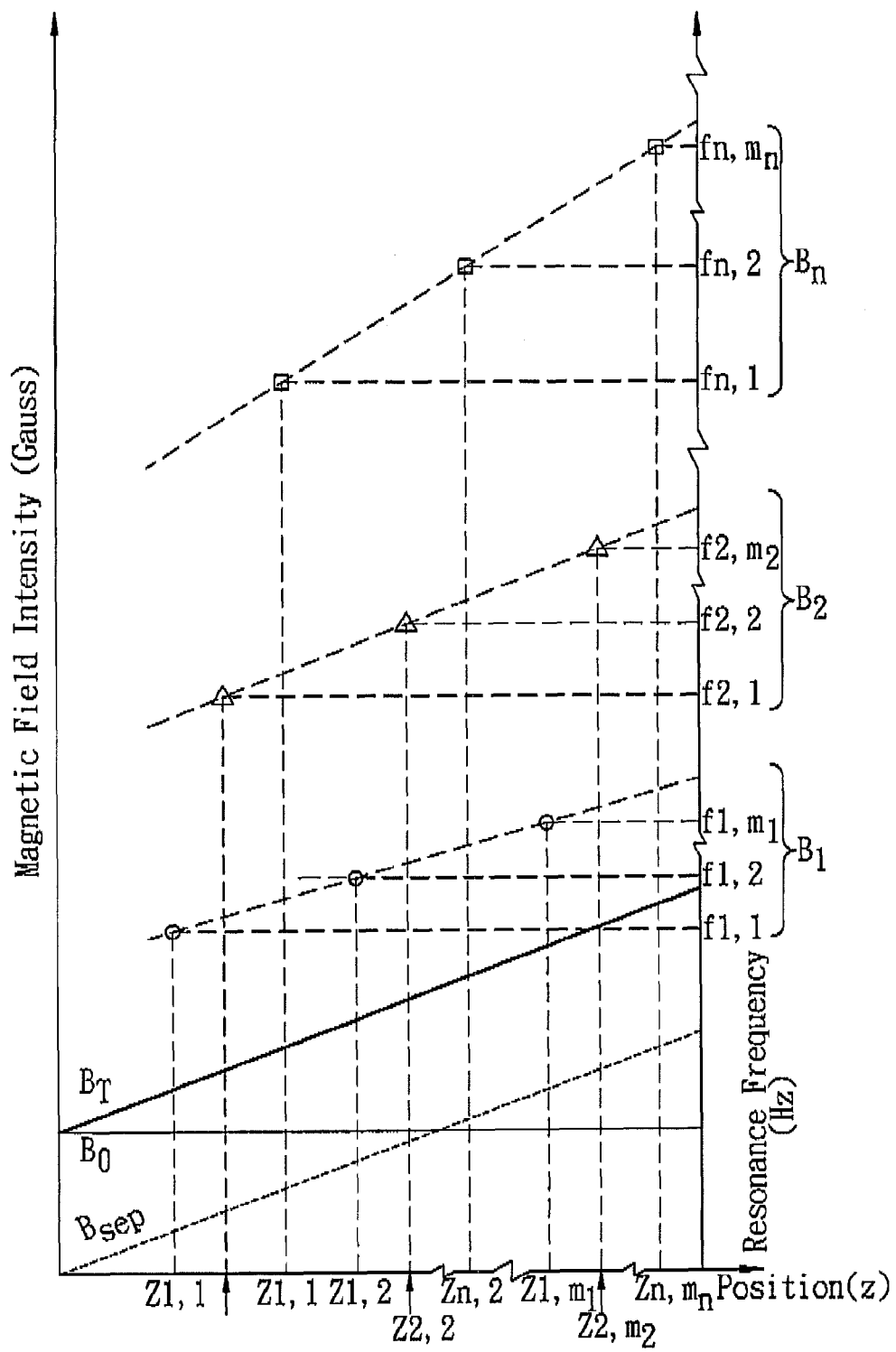
F I G. 7A

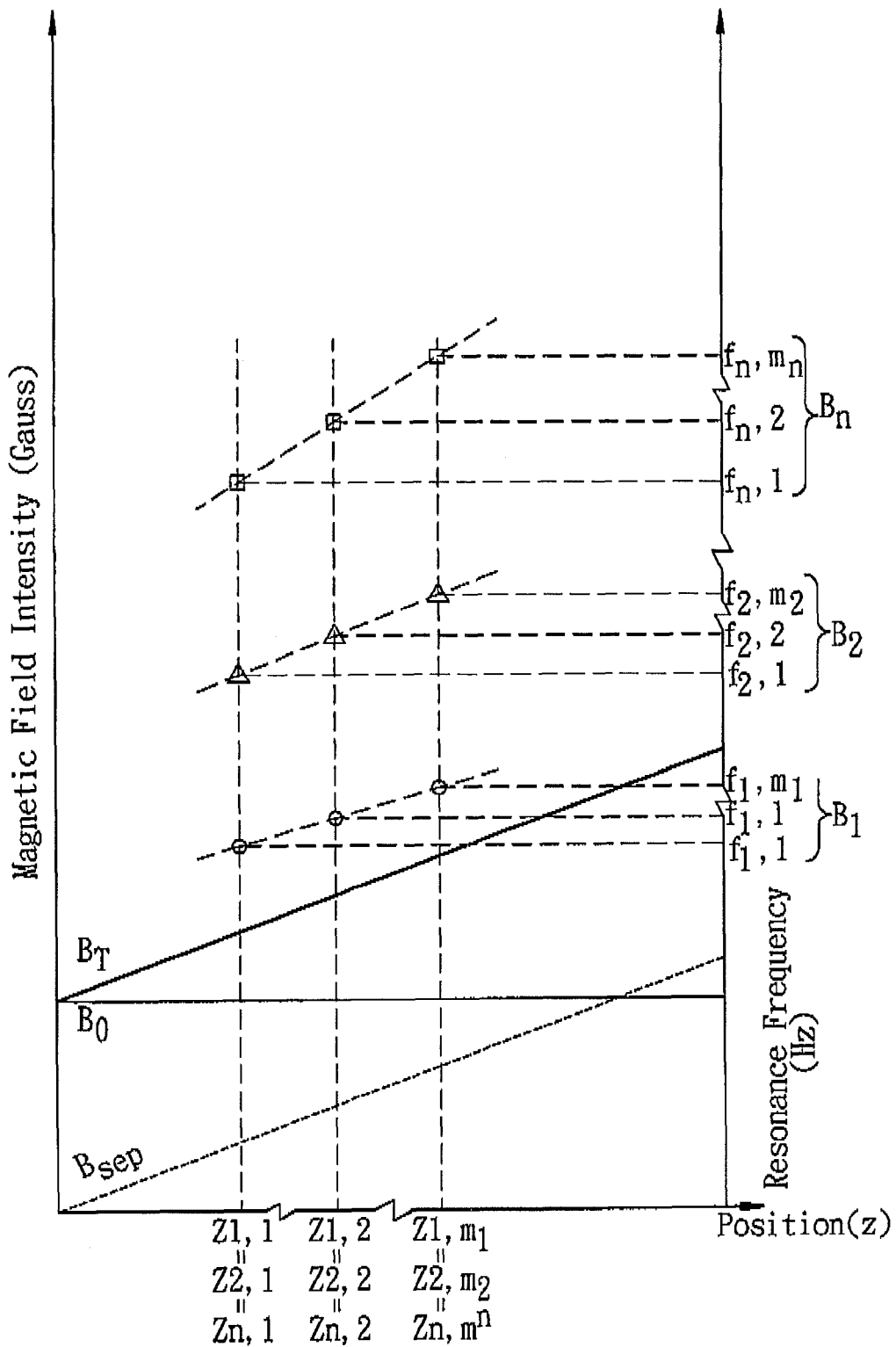
F I G. 7B

1210 — PERFORMING A PLURALITY OF DATA COLLECTION SEQUENCES, WHEREIN EACH DATA COLLECTION SEQUENCE INCLUDES APPLYING AN EXCITATION RADIO FREQUENCY SIGNAL AND A SELECTION GRADIENT, THE EXCITATION RADIO FREQUENCY SIGNAL INCLUDING A FIRST SET OF FREQUENCY BANDS SELECTED TO SIMULTANEOUSLY EXCITE A FIRST NUCLEI TYPE IN A PLURALITY OF CROSS-SECTIONS OF A SUBJECT, APPLYING A DIFFUSION GRADIENT DURING FORMATION OF A MAGNETIC RESONANCE SIGNAL, APPLYING A SPATIAL ENCODING GRADIENT DURING FORMATION OF THE MAGNETIC RESONANCE SIGNAL, AND WHILE ACQUIRING THE MAGNETIC RESONANCE SIGNAL, APPLYING A SEPARATION GRADIENT TO CHANGE A FREQUENCY SEPARATION BETWEEN PORTIONS OF THE MAGNETIC RESONANCE SIGNAL

1220 — COMPUTATIONALLY DETERMINING A DIFFUSION IMAGE OF EACH OF THE PLURALITY OF CROSS SECTIONS AS A FUNCTION OF A DATA SET OF EACH OF THE PLURALITY OF DATA COLLECTION SEQUENCES AND A GYROMAGNETIC RATIO OF THE FIRST NUCLEI TYPE, EACH DATA SET INCLUDING A RESPECTIVE MAGNETIC RESONANCE SIGNAL, A RESPECTIVE SEPARATION GRADIENT, AND A RESPECTIVE DIFFUSION GRADIENT

F I G. 12

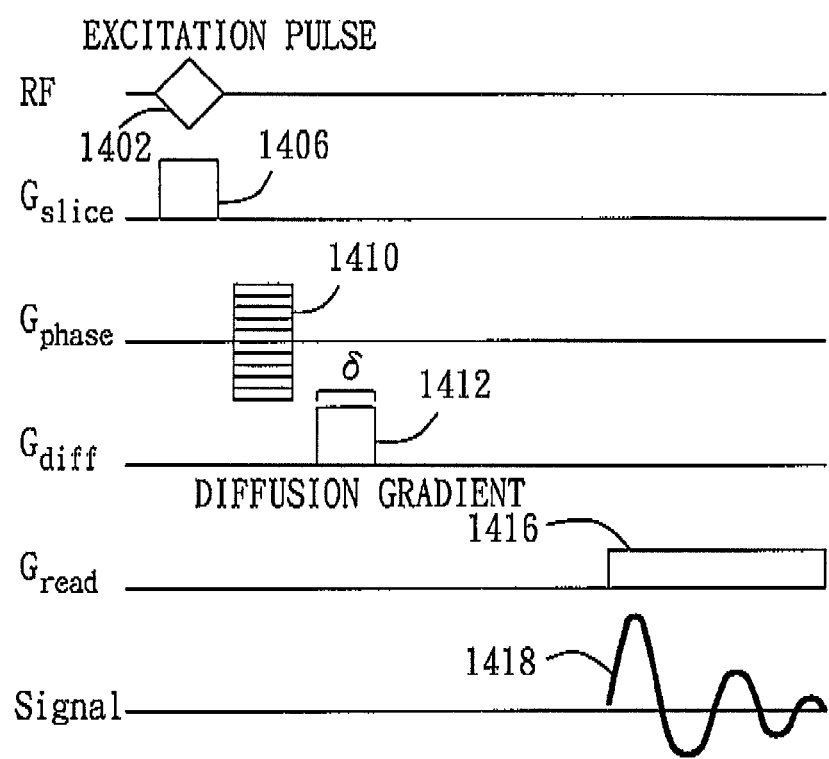
F I G. 14

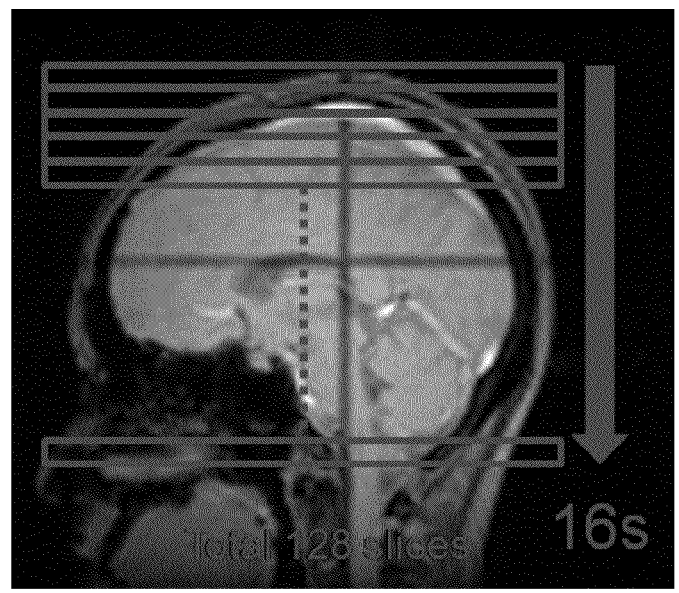
F I G. 15A
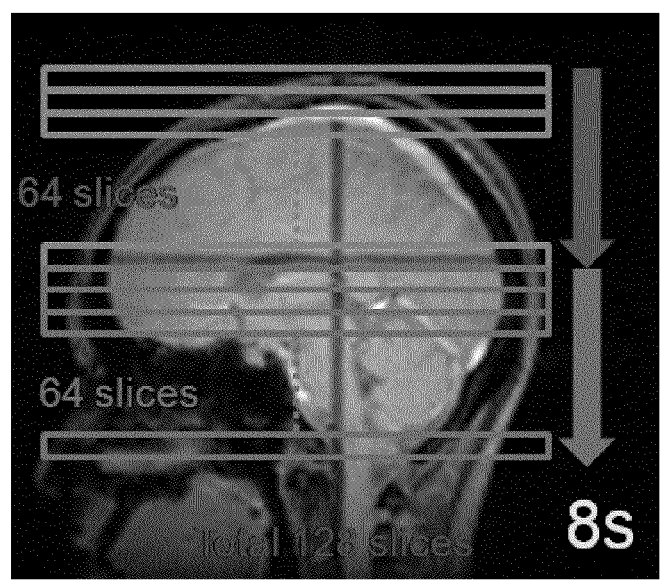
F I G. 15B

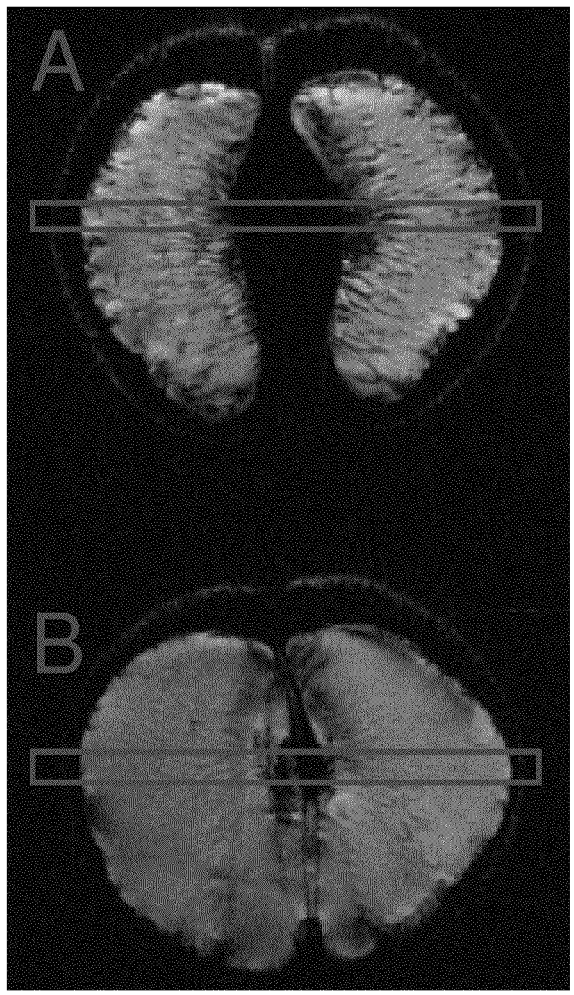 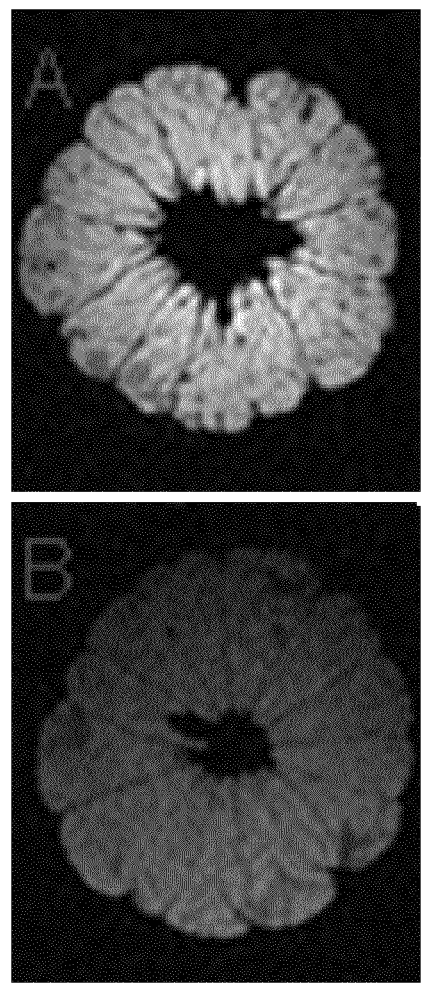
F I G. 16A  F I G. 16B

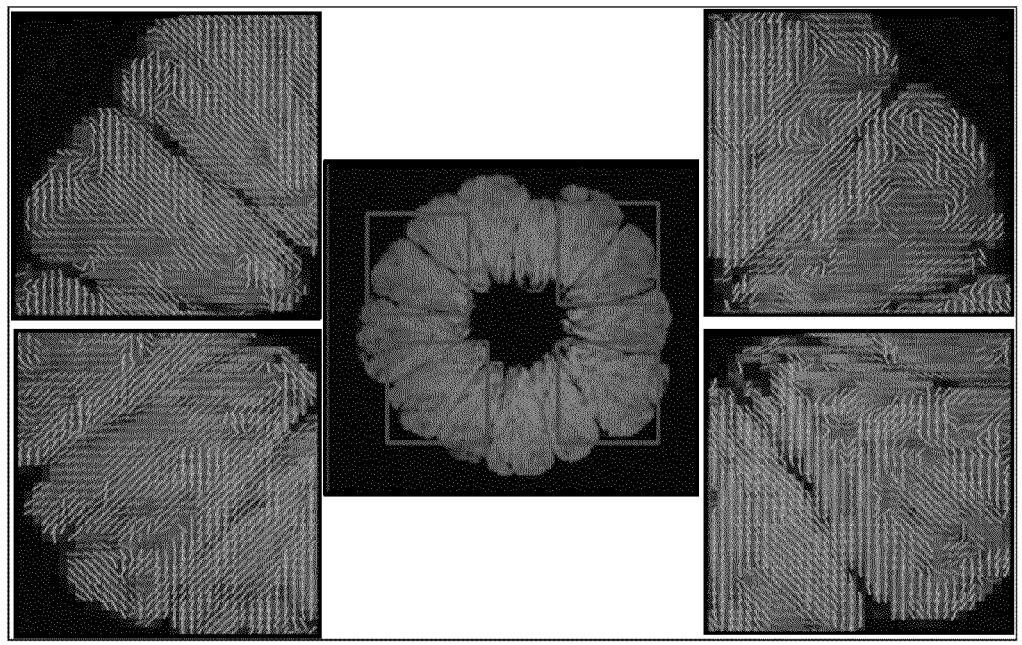
F I G. 17

US 8,664,952 B2

SIMULTANEOUS DIFFUSION IMAGING OF MULTIPLE CROSS SECTIONS

CROSS-REFERENCES TO RELATED APPLICATIONS

The present application claims the benefit of U.S. provisional patent application No. 61/325,657, filed on Apr. 19, 2010. The present application is further a continuation in part of U.S. patent application Ser. No. 12/370,214, filed on Feb. 12, 2011, entitled "Wideband Magnetic Resonance Imaging Apparatus and Method," which is a continuation in part of U.S. patent application Ser. No. 12/337,388, filed on Dec. 17, 2008, entitled "Method and Apparatus for Simultaneously Acquiring Multiple Slices/Slabs in Magnetic Resonance System." The applications identified above are each incorporated herein by reference in their entirety as if set forth in full.

BACKGROUND

1. Technical Field

The embodiments described herein relate to a diffusion imaging method, and more particularly, to simultaneous diffusion imaging of multiple cross sections.

2. Related Art

Conventional diffusion imaging may be performed by sequentially exciting one cross section of a subject at a time. Completing an imaging process using conventional diffusion imaging may require an excessive amount of time, which may increase an imaging cost and may subsequently reduce a likelihood of successfully treating a patient or performing research.

SUMMARY

In an aspect, a diffusion imaging method comprises performing a plurality of data collection sequences. Each data collection sequence includes applying an excitation radio frequency signal and a selection gradient. The excitation radio frequency signal includes a first set of frequency bands selected to simultaneously excite a first nuclei type in a plurality of cross sections of a subject. Each data collection sequence further includes applying a diffusion gradient during formation of a magnetic resonance signal, applying a spatial encoding gradient during formation of the magnetic resonance signal, and while acquiring the magnetic resonance signal, applying a separation gradient to change a frequency separation between portions of the magnetic resonance signal. The diffusion imaging method further comprises computationally determining a diffusion image of each of the plurality of cross sections as a function of a data set of each of the plurality of data collection sequences and a gyromagnetic ratio of the first nuclei type. Each data set includes a respective magnetic resonance signal, a respective separation gradient, and a respective diffusion gradient.

These and other features, aspects, and embodiments are described below in the section entitled "Detailed Description."

BRIEF DESCRIPTION OF THE DRAWINGS

Features, aspects, and embodiments are described in conjunction with the attached drawings, in which:

FIG. 1 is a table summarizing the gyromagnetic ratios for some exemplary kinds of nuclei;

FIG. 2 is a diagram illustrating the configuration of an exemplary wideband MRI apparatus in accordance with one embodiment;

FIGS. 7A and 7B are exemplary diagrams showing the relationship between the frequency component distribution and slice/slab location distribution in accordance with two different embodiments;

FIG. 12 is a process flow of simultaneous diffusion imaging of multiple cross sections, according to one embodiment;

FIG. 14 is a timing diagram of simultaneous diffusion imaging of multiple cross sections using a spin echo in accordance with one embodiment;

FIGS. 15A and 15B illustrate reducing scanning time through simultaneous diffusion imaging of multiple cross sections in accordance with one embodiment;

FIG. 16 is an illustration of simultaneous diffusion imaging of two cross sections in accordance with one embodiment; and FIG. 17 is an illustration of an eigenvector map of a cross section acquired in accordance with one embodiment.

DETAILED DESCRIPTION

Figure 3:
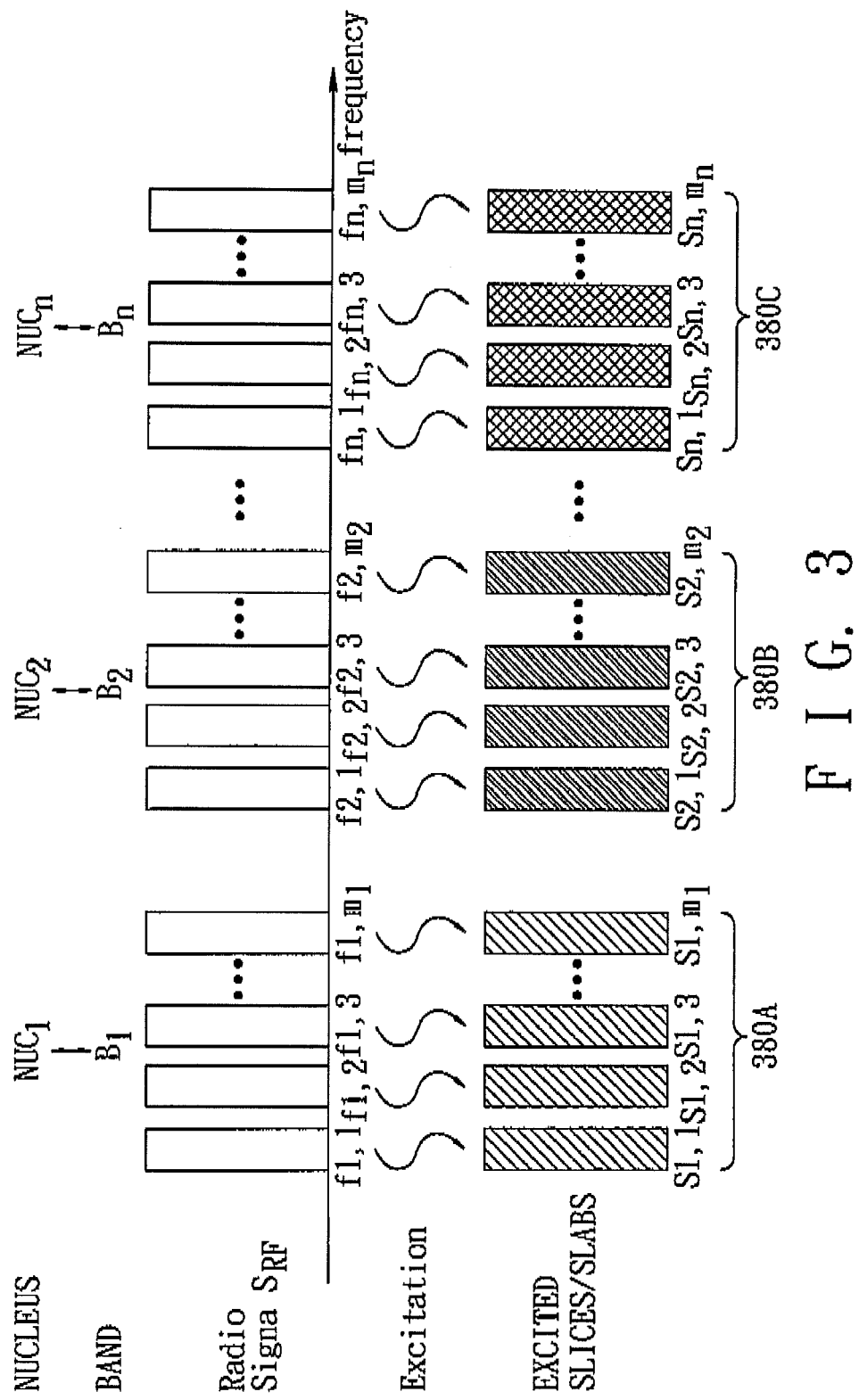
FIG. 3 is an exemplary diagram illustrating the frequency distribution of an RF signal in accordance with one embodiment.

FIG. 2 is a diagram illustrating the configuration of an exemplary wideband MRI apparatus 200 in accordance with one embodiment, capable of simultaneously acquiring MR images for different kinds of nuclei. As shown, the wideband MRI apparatus 200 comprises a sequence controller 210, a static magnetic field output module 220, a radio frequency (RF) system 230 that has an RF excitation module 232 and an RF receiving module 234, and a gradient output module 240 that has a gradient controller 242 and a plurality of gradient coils 244 controlled by the gradient controller 242. Additionally, the wideband MRI apparatus 200 can also comprise a main console 250 that has a control module 252, a storage module 254, and an imaging processing module 256. Moreover, the wideband MRI apparatus 200 can further comprise a display device 260 and an input device 270.

The control module 252, a computer for example, can be configured to control the sequence controller 210, the storage module 254, the imaging processing module 256, the display device 260, and the input device 270 to carry out MRI operation, by executing and accessing several programs and data stored in the storage module 270, e.g., a memory. During an MRI operation, the sequence controller 210, responsive to the control module 252, can control the RF system 230 and the gradient output module 240 to sequentially perform an excitation procedure and a reception procedure. After the excitation and reception procedures, the imaging processing module 256 and the display device 260 can then perform an image reconstruction procedure in response to the control module 252, reconstructing data acquired in the reception procedure to display reconstructed images. Additionally, a user can interactively operate the wideband MRI apparatus 200 and set several physical quantities via communication with the control module 200 by using the display device 260, e.g., a graphic display, and the input device 270, e.g., a keyboard. The imaging operation of the wideband MRI apparatus 200 during the excitation, reception, and image-reconstruction procedures is detailed below.

1. Excitation Procedure

The static magnetic field output module 220 can be configured to generate a static and uniform magnetic field $B_0$ in a measuring space 4 in which resides a subject 2, e.g., a living body or part of a living body, to be scanned. The direction of the static magnetic field, for example, is along a z-axis.

The RF excitation module 232 in the RF system 230, responsive to the sequence controller 210, can generate a wideband RF signal that has a plurality of frequency bands respectively corresponding to a plurality of different kinds of nuclei, and transmit the RF signal to the measurement space 4 for simultaneously exciting the different kinds of nuclei within the subject 2. The frequency difference between different frequency bands, for example, can be as large as several MHzs or several tens of MHzs, depending on the kinds of nuclei to be excited.

FIG. 3 is an exemplary diagram illustrating the frequency distribution of the RF signal that can be generated by the RF excitation module 220 in FIG. 2 in accordance with one embodiment. As shown, the RF signal has a plurality of frequency bands $B_1, B_2, \ldots,$ and $B_n$ (n is an integer and $2 \le n$) that correspond to a plurality of different kinds of nuclei $NUC_1, NUC_2, \ldots,$ and $NUC_n$, respectively. Moreover, each of the frequency bands, $B_i$ (i is an integer and i=1~n), can include one or more frequency components fi, 1–fi,$m_i$ ($m_i$ is an integer and $m_i \ge 1$ for each i) that are equal, or close to the resonance frequencies of a corresponding kind of nuclei $NUC_i$ at excitation positions. Accordingly, one or more frequency components fi, 1–fi, $m_i$ within each frequency band $B_i$ can be used to excite one or more slices/slabs Si, 1–Si,$m_i$, respectively.

Referring back to FIG. 2, the RF excitation module 230, for example, can include a single RF transmission coil element (not shown) capable of irradiating the wideband RF signal that has the different frequency bands respectively corresponding to the different kinds of nuclei. Alternatively, the RF excitation module 230 can otherwise include a plurality of RF transmission coil elements (not shown), each simultaneously irradiating a respective RF signal that has one or more frequency bands for exciting the corresponding kind(s) of nuclei. Because the frequency differences between different frequency bands can be large, a coupling reduction mechanism between the coil elements may not be required in some embodiments. However, the coupling reduction mechanism may also be implemented to prevent interference between different frequency bands in some other mechanism if required.

When the RF signal generated by the RF excitation module 230 is applied, the gradient controller 242, responsive to the sequence controller 210, can control the gradient coils 242 to generate and transmit a slice/slab selection gradient $G_{ss}$ slice for 2D and slab for 3D, to the measurement space 4. The slice/slab selection gradient $G_{ss}$ can be a magnetic field gradient serving to select the excitation location(s) for the slice(s)/slab(s) for each kind of nucleus. Described in more detail, the slice/slab selection gradient $G_{ss}$ can be used to add spatial variation to the uniform magnetic field $B_0$ generated by the static magnetic field output module 220, such that the same kind of nuclei at different positions can have different resonance frequencies at different positions, and one or more frequency components within each frequency band of the RF signal can therefore simultaneously excite one kind of nucleus corresponding to the frequency band at selected excitation location(s) corresponding to the frequency component(s).

Figure 4:
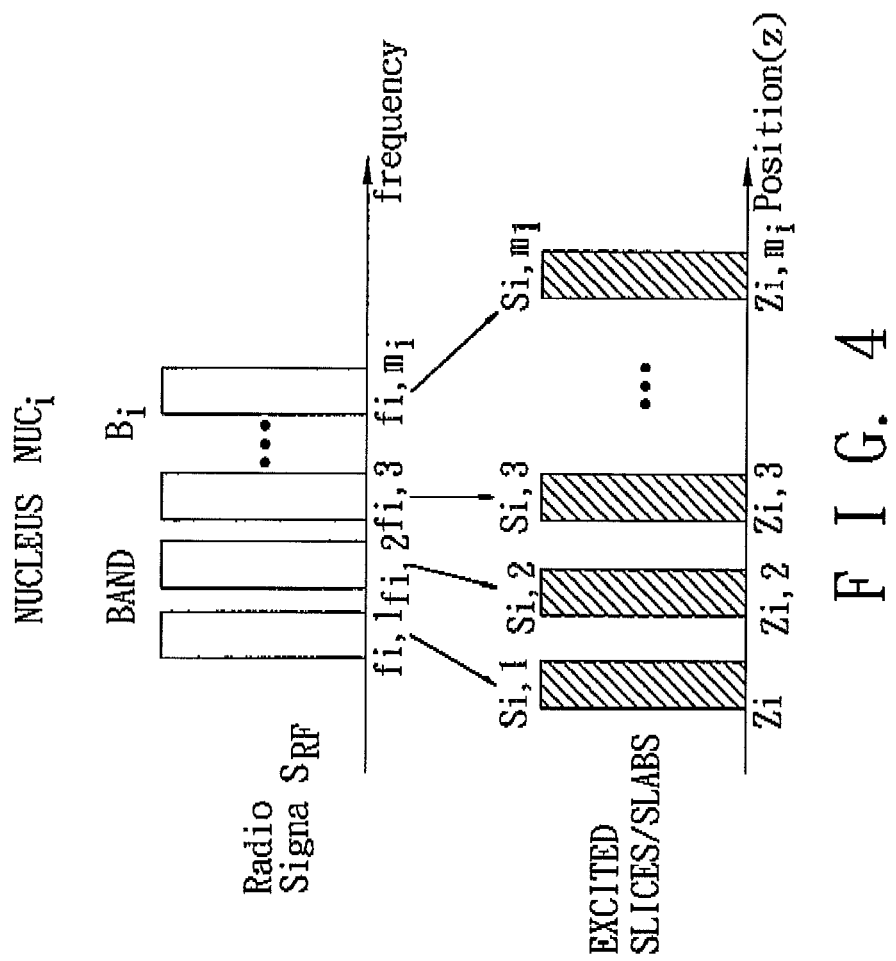
FIG. 4 is a schematic diagram illustrating the correspondence between the frequency component(s) in a frequency band and the excitation location(s) of the slice(s)/slab(s)

FIG. 4 is a schematic diagram illustrating the correspondence between the frequency component(s) in a frequency band and the excitation location(s) of the slice(s)/slab(s). As shown in FIG. 3, the frequency components fi, 1, fi, 2, ..., and fi,$m_i$ in a frequency band $B_i$ (i is an integer and i=1~n) can be used to excite one or more slices/slabs Si, 1, Si, 2, ..., and Si,$m_i$, respectively, which have respective positions of zi, 1, zi, 2, ..., and zi,mi. It is noted that a single frequency band $B_i$ can be used to excite a single slice/slab or multiple slice/slabs, depending on whether the frequency band $B_i$ has a single or multiple frequencies.

Figure 5A:
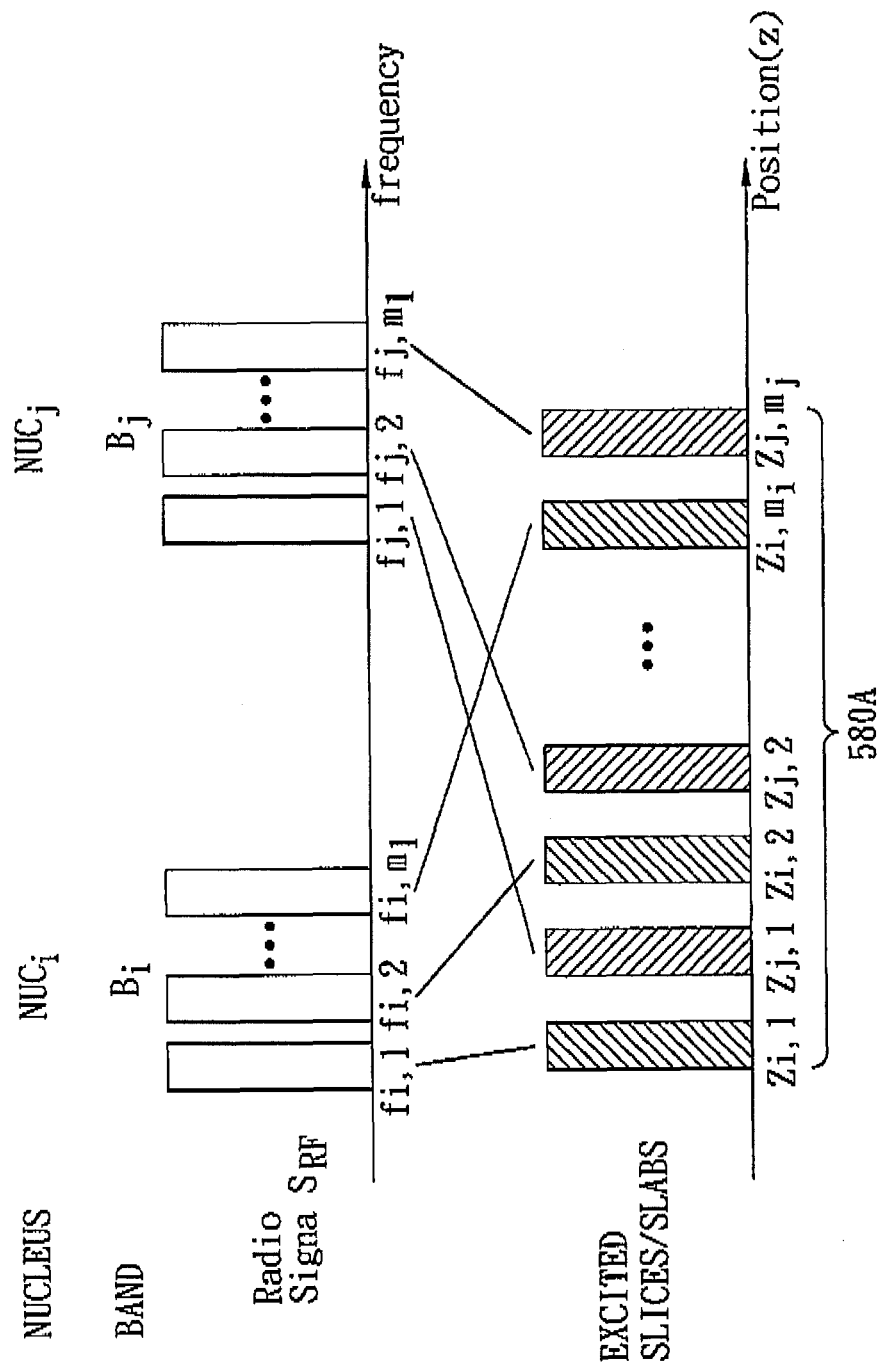
FIGS. 5A and 5B are diagrams schematically illustrating the excitation location distribution of the slices/Slabs for different kinds of nuclei according to two different embodiments.
Figure 5B:
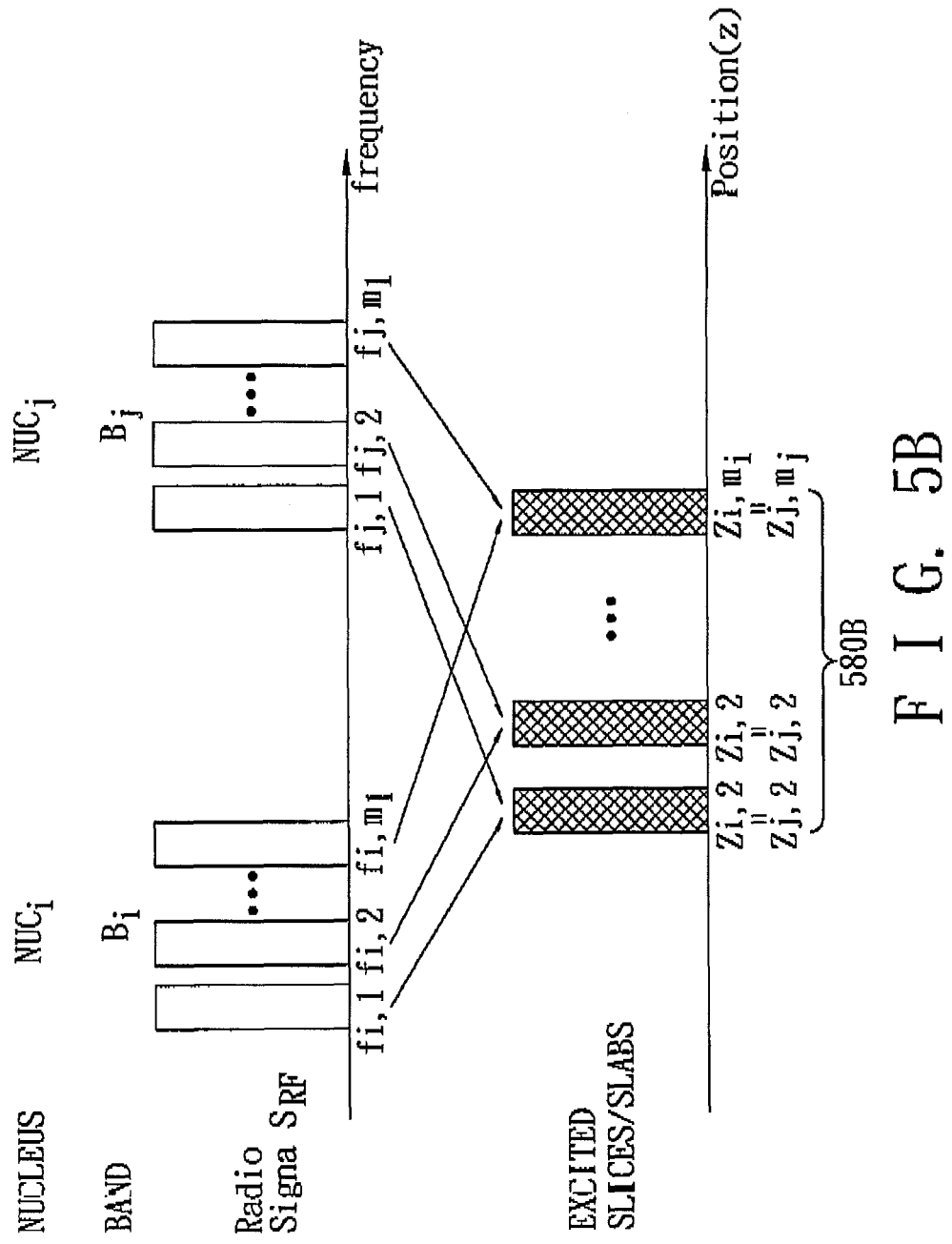

Additionally, it is also noted that the slices/slabs for different kinds of nuclei can be at the same or different excitation locations, as is shown with FIGS. 5A and 5B, respectively, which are diagrams schematically illustrating the excitation locations distribution of the slices/slabs for different kinds of nuclei in accordance with two different embodiments. In FIG. 5A, two different frequency bands Bi and Bj (j is an integer and i≠j) excite their respective slice(s)/slab (s) at different locations, as is referred hereafter to as "multiple slices/slabs for multiple nuclei". In FIG. 5B, two different frequency bands $B_i$ and $B_j$ (j is an integer and i≠j) excite their respective slice(s)/slab (s) at the same location (s), as is referred hereafter to as "single slice/slab for multiple nuclei".

The slice/slab selection gradient $G_{ss}$, in accordance with one specific embodiment, can be a time-invariant, i.e., static, gradient magnetic field varied linearly along a slice/slab selection direction, which, preferably, can be parallel with the static magnetic field direction, i.e., the z-axis in the embodiment. The slice/slab selection gradient $G_{ss}$ can therefore be expressed as $G_{ss} z$, where $G_{ss}$ denotes the intensity, e.g., in Gauss/centimeter, of the slice/slab selection gradient $G_{ss}$, and z denotes the position along the z-axis. However, various other slice/slab selection gradients can also be used in alternative embodiments.

Figure 6:
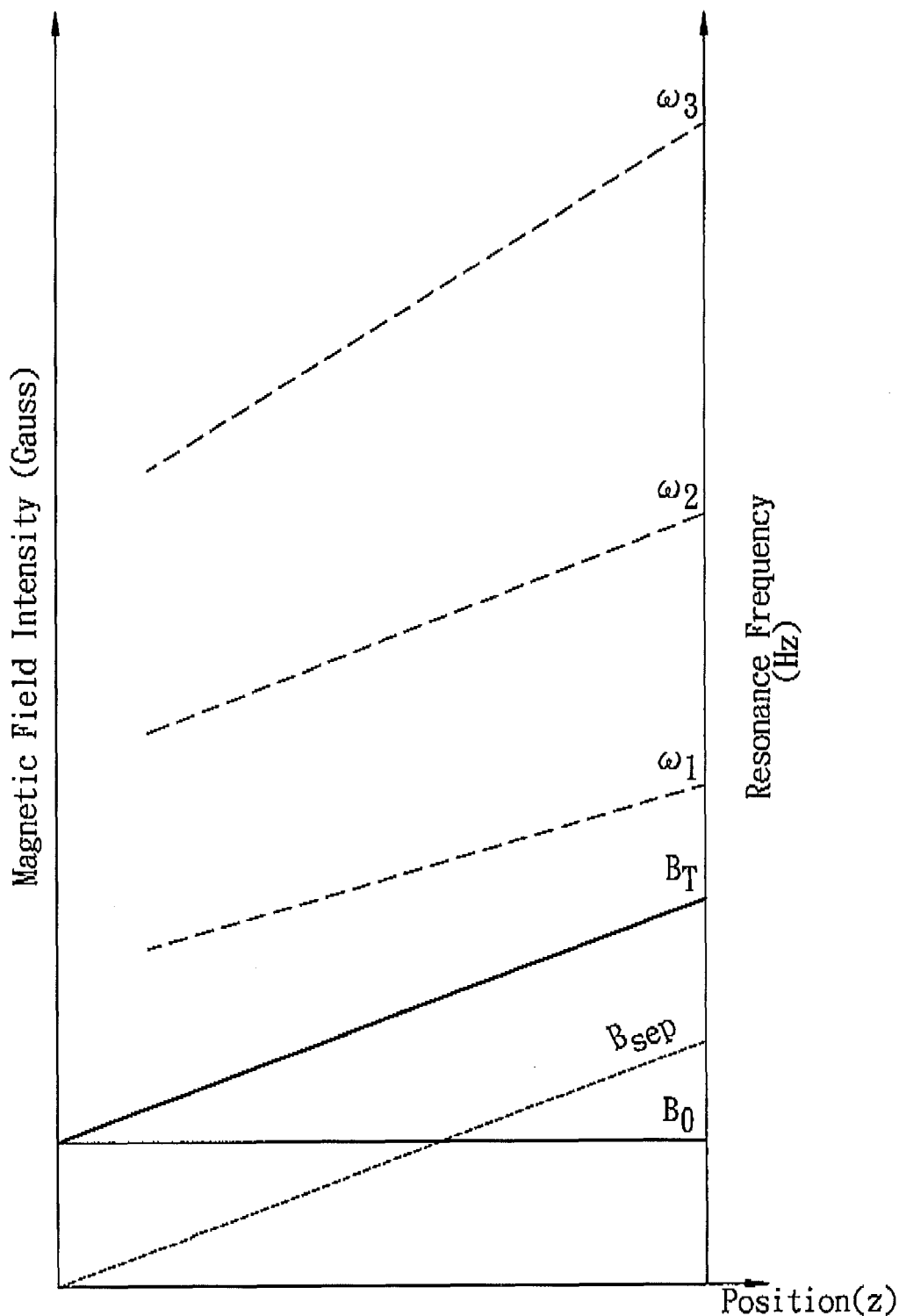
FIG. 6 is an exemplary diagram showing magnetic fields and the resonance frequencies for different kinds of nuclei as a function of position in accordance with one embodiment.

FIG. 6 is an exemplary diagram showing the dependence among the static magnetic field $B_0$, the slice/slab selection gradient $G_{ss}$, and the total magnetic field $B_T$, as a function of the position in the measuring space 230, in accordance with one specific embodiment with a time-invariant linear slice/slab selection gradient $G_{ss}$. FIG. 6 further shows the resonance frequencies for different kinds of nuclei under the total magnetic field $B_T$ as a function of the position, for explaining the principle behind the slice/slab selection gradient $G_{ss}$.

Referring to FIG. 6, the total magnetic field $B_T$ in the measuring space 4, being the static magnetic field $B_0$ plus the variation due to the slice/slab selection gradient $G_{ss}$, is a time-invariant gradient magnetic field linearly varied along the slice/slab selection direction, expressed as $B_T=B_0+G_{ss}z$. Under such a total magnetic field $B_T$, the resonance frequency of a nucleus, or the required frequency to excite the nuclei, therefore depends both on the kind and the position of the nucleus, as can be mathematically expressed;

$$\omega_i(z)=(B_0+G_{ss}z)\times\gamma_i, \quad (Eq. 1)$$

where $\omega_i(z)$ denotes the resonance frequency of a nucleus $NUC_i$ at position z, and $\gamma_i$ denotes the atomic gyromagnetic ratio of the nucleus $NUC_1$.

FIGS. 7A and 7B are exemplary diagrams showing the relationship between the frequency component distribution within each frequency band of the RF signal and its corresponding slice/slab location distribution in the measuring space 4, in accordance with two different embodiments. FIGS. 7A and 7B, respectively corresponding to FIGS. 5A and 5B, show two cases where different kinds of nuclei NUC1-NUCn are excited at the same and different excitation locations.

Referring both to FIGS. 7A and 7B, due to the nuclei kind factor, i.e., $\gamma_i$, in $\omega_i(z)$, different kinds of nuclei $NUC_1$-$NUC_n$ are required to be excited with different frequency bands B1-Bn corresponding to the atomic gyromagnetic ratios $\gamma_1$-$\gamma_n$ of the different kinds of nuclei $NUC_1$-$NUC_n$.

Moreover, due to the position factor, i.e., z, in $\omega_i(z)$, for each kind of nucleus $NUC_i$ (i is an integer and i=1~n), one or more slice(s)/slab(s) Si, 1-Si,$m_i$ ($m_i$ is an integer and $m_i \geq 1$ for each i) are required to be excited with one or more frequency component(s) fi, 1-fi,$m_i$ corresponding to the position (s) zi, 1-zi, $m_i$ of the slice(s)/slab(s) Si, 1-Si,$m_i$.

More specifically, the frequency difference between any two neighboring frequency components fi, k and fi, (k+1) (k is an integer and k=1~$m_i$) within the frequency band $B_i$ can be determined according both to the absolute distance |zi, k-zi, (k+1)| between two neighboring slices/slabs Si, k and Si, (k+1) and the atomic gyromagnetic ratio of the nucleus $NUC_i$ according to an equation:

$$f_{sep,i}=d_{sep,i}\times\gamma_i\times G_{ss}, \quad (Eq. 2)$$

where $f_{sep,i}$ denotes the frequency difference, i.e., $f_{sep,i}$=|fi, k-fi, (k+1)|, e.g., in Hz; $d_{sep,i}$ denotes the absolute distance between two neighboring slices/slabs for nucleus $NUC_i$, i.e., $d_{sep,i}$=|zi, k-zi, (k+1)|, e.g., in centimeters, that, for example, is set by the user according to practical needs; $\gamma_i$ denotes the atomic gyromagnetic ratio of nucleus $NUC_i$; and $G_{ss}$ denotes the intensity of the slice/slab selection gradient $G_{ss}$, e.g., in Gauss/centimeter.

Accordingly, the respective frequency components fi, 1-fi, $m_i$ in each frequency band $B_i$ can be determined according to Eq. 2 to acquire a desired slice/slab location distribution. In addition, the respective frequency components fi, 1-fi,$m_i$ and fj, 1-fj $m_j$ (j is an integer and i≠j) in frequency bands Bi and Bj can have a configuration of multiple slices/slabs for multiple nuclei, meaning that the corresponding slice/slab locations zi, 1-zi,$m_i$ are different from zj, 1-zj,$m_j$, as shown in FIG. 7A, or alternatively, can otherwise have a configuration of single slice/slab for multiple nuclei, meaning that the corresponding slice/slab locations zi, 1-zi,$m_i$ are equal to zj, 1-zj,$m_j$, as shown in FIG. 7B.

Because the RE excitation module is capable of generating a wideband RF signal, the wideband MRI apparatus 200 can simultaneously excite different kinds of nuclei within the subject at the same or different locations without any switching mechanism between different frequency bands, thus accelerating the excitation procedure.

2. Reception Procedure

The RF receiving module 234 in the RF system, responsive to the sequence controller 210, can be configured to detect a responsive RF signal, e.g., the "free induction decay (FID) signal," generated by the different excited nuclei. The FID signal, similar to the RF signal generated by the RF excitation module 230, can also be a wideband signal having a plurality of frequency bands that are respectively emitted by the different kinds of nuclei when relaxing from excitation states to lower energy states.

Specifically, the RF receiving module 234 can simultaneously receive and process, e.g., amplify, demodulate, filter, and digitize, the different frequency bands within the RF signal, and then provide digital data to the control module, which further transmits the digital data to the imaging processing module, or alternatively, directly provide the digital data to the imaging processing module. The digital data can also be stored in the storage module 254 if required. The digital data represent the MR images in frequency space, or Fourier space or k space.

The RF receiving module 234, for example, can include a single RF reception coil element (not shown) capable of simultaneously detecting different frequency bands within the wideband FID signal generated by different kinds of nuclei. Alternatively, the RF receiving module can include a plurality of RF reception coil elements, each simultaneously detecting one or more frequency bands emitted by corresponding kind(s) of nuclei. Because the frequency differences between different frequency bands can be large, coupling reduction mechanism between the coil elements may not be required in some embodiments; however, a coupling reduction mechanism may also be implemented to prevent interference between different frequency bands in some other mechanism if required.

It should be noted that the RF excitation module 232 and the RF receiving module 234 are not required to be disposed separately. In other embodiments, the RF excitation module 232 and the RF receiving module 234 can be integrated as a single RF excitation/receiving module (not shown). Specifically, the single RF excitation/receiving module, for example, can include a single RF transmission/reception coil element capable of transmitting and receiving a wideband RF signal. Alternatively, the single RF excitation/receiving module can include a plurality of RF transmission/reception coil elements, each simultaneously transmitting and receiving one or more frequency bands corresponding to one or more kinds of nuclei.

The gradient controller 242, responsive to the sequence controller 252, can control the gradient coils 242 to generate and transmit a spatial encoding gradient $G_{enc}$ and a slice/slab separation gradient $G_{sep}$, slice for 2D and slab for 3D, to the measurement space 4. The spatial encoding gradient $G_{enc}$ and the slice/slab separation gradient $G_{sep}$ are used to add spatial information in different directions to the FID signal generated by the RF receiving module.

The spatial encoding gradient is a magnetic field gradient serving to encode the responsive RF received by the RF receiving module 234. Specifically, the spatial encoding gradient $G_{enc}$ comprises a phase-encoding gradient $G_p$ applied to phase-encode the responsive RF signal and a frequency-encoding gradient $G_f$ applied to frequency-encode the responsive RF signal.

On the other hand, the slice/slab separation gradient $G_{sep}$ is a magnetic field gradient serving to separate any two neighboring frequency components in each frequency band in the FID signal received by the RF receiving module, or effectively, to separate any two neighboring slices/slices for each kind of nucleus. The slice/slab separation gradient $G_{sep}$, for example, can be a time-invariant gradient magnetic field linearly varied along a slice/slab separation direction, which, for example, can be parallel with the normal direction of the slices/slabs, i.e. the z-axis in the embodiment.

In accordance with one 2D embodiment, the phase-encoding gradient $G_p$ may be implemented as a magnetic field gradient along a phase-encoding direction, e.g., a y-axis, here denoted as $G_p=Gy$. The frequency-encoding gradient $G_f$ may be implemented as a magnetic field gradient along a frequency-encoding direction, e.g., an x-axis, here denoted as $G_f=G_x$. There can be a variety of generation sequences of the gradients. For example, when the RF receiving module receives the FID signal, the gradient output module can simultaneously generate the phase-encoding gradient, i.e., $G_y$, the frequency-encoding gradient, i.e., $G_x$, and the slice separation gradient $G_{sep}$. The spatial encoding gradient when generated simultaneously with the slice/slab separation gradient $G_{sep}$, is hereafter denoted as $G_{spen}$, i.e., $G_{spen}=G_x+G_y$ in the example. In another example, the gradient output module can first generate the phase-encoding gradient, i.e., $G_y$. Then, the RF receiving module receives the FID signal while the gradient output module simultaneously generates the frequency-encoding gradient, i.e., $G_{spen}=Gf=G_x$, and the slice separation gradient $G_{sep}$. A similar procedure can be repeated several times, referred to as the number of the spatial encoding, with different intensities of the phase-encoding gradient $G_p=G_y$.

In accordance with one 3D embodiment, the phase-encoding gradient may be implemented as two magnetic fields along two phase-encoding directions, e.g., along a y-axis and the z-axis, here denoted as $G_p=G_y+G_z$. The frequency-encoding gradient may be implemented as a magnetic field along a frequency-encoding direction, e.g., along an x-axis, here denoted as $G_f=G_x$. There can be a variety of generation sequences of the gradients. For example, the gradient output module can first generate the phase-encoding gradient, i.e., $G_y+G_z$. And then, the RF receiving module is activated to receive the FID signal, while the gradient output module simultaneously generates the frequency-encoding gradient, i.e., $G_{spen}=Gf=G_x$, and the slice separation gradient $G_{sep}$ along the z-axis. A similar procedure can be repeated several times, referred to as the number of the spatial encoding, with different intensities of the phase-encoding gradient $G_p$, that is, different intensity combinations of $G_y$ and $G_z$.

Figure 8:
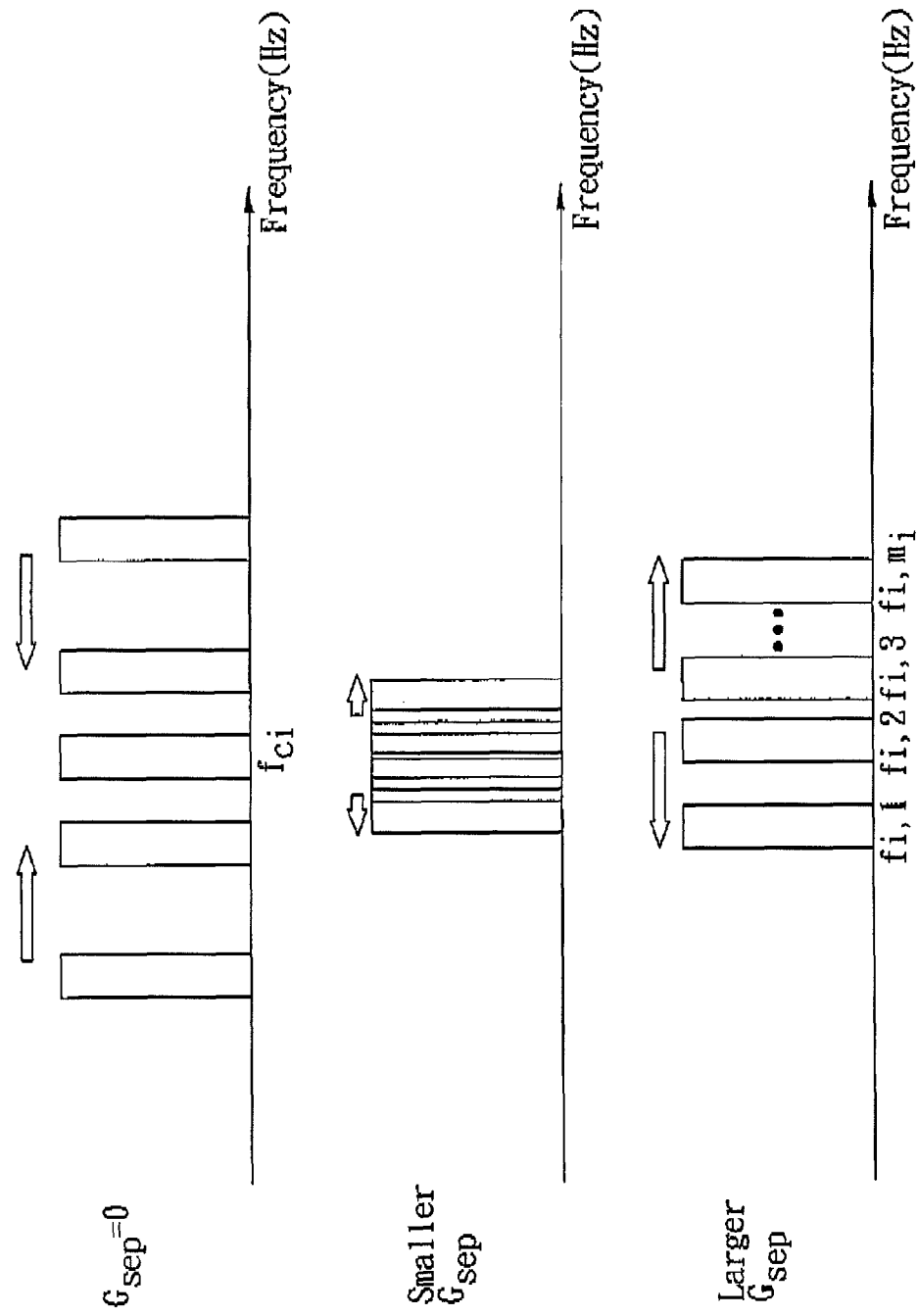
FIG. 8 is an exemplary diagram schematically illustrating the separation of neighboring frequency components of the FID signal under different intensities of the slice/slab separation gradient in accordance with one embodiment.

FIG. 8 is an exemplary diagram schematically illustrating the separation of neighboring frequency components in a frequency band of the FID signal received by the RF receiving module 234 under different intensities of the slice/slab separation gradient $G_{sep}$ in accordance with one embodiment. As shown, different frequency components in a frequency band $B_i$ (i=1~n) of the received FID signal, if without the slice/slab separation gradient $G_{sep}$, would be overlapped completely at a center frequency $f_{ci}$ of the frequency band $B_i$. With the increase of the intensity of the slice/slab separation gradient $G_{sep}$, neighboring slices/slices can be more separated from each other.

Regarding determination of the intensities of time-invariant and linear slice/slab separation gradient $G_{sep}$ and the spatial encoding gradient $G_{spen}$ in accordance with one specific embodiment, their intensity dependency can be satisfied by an equation:

$$G_{sep}/G_{spen} \geq FOV_{spen}/d_{sep,i}, \quad \text{(Eq. 3)}$$

where $G_{sep}$ denotes the intensity of the slice/slab separation gradient $G_{sep}$, e.g., in Gauss/centimeter; $G_{spen}$ denotes the intensity of the spatial encoding gradient $G_{spen}$, e.g., in Gauss/centimeter, which may be the intensity of $G_x+G_y$, $G_x$, or $G_y$, depending on the generation sequences of the gradients; $FOV_{spen}$ denotes a field of view, e.g., width and in centimeters, along the direction of the spatial encoding gradient $G_{spen}$ that, for example, is set according to practical needs; and $d_{sep,i}$ denotes the absolute distance between two neighboring slices/slabs for nucleus $NUC_i$, e.g., in centimeters, that, for example, is set according to practical needs.

One unique feature of the invention is that, because the RF receiving module is capable of receiving a wideband FID signal, the wideband MRI apparatus 200 can simultaneously detect relaxation energy released by different kinds of nuclei without any switching mechanism between different frequency bands, thus accelerating the reception procedure.

3. Image Reconstruction Procedure

After the imaging processing module 256 receives the digital data, it then performs transformation, e.g., 2D/3D Fourier Transform, on the digital data in frequency space to reconstruct real-time MR images in real space The digital data in the frequency space are also wideband data, including data for a plurality of frequency bands corresponding to the different kinds of nuclei. Consequently, MR images for the different kinds of nuclei can also be simultaneously acquired. The display device 260 can then display the reconstructed real-time MR images.

Figure 9:
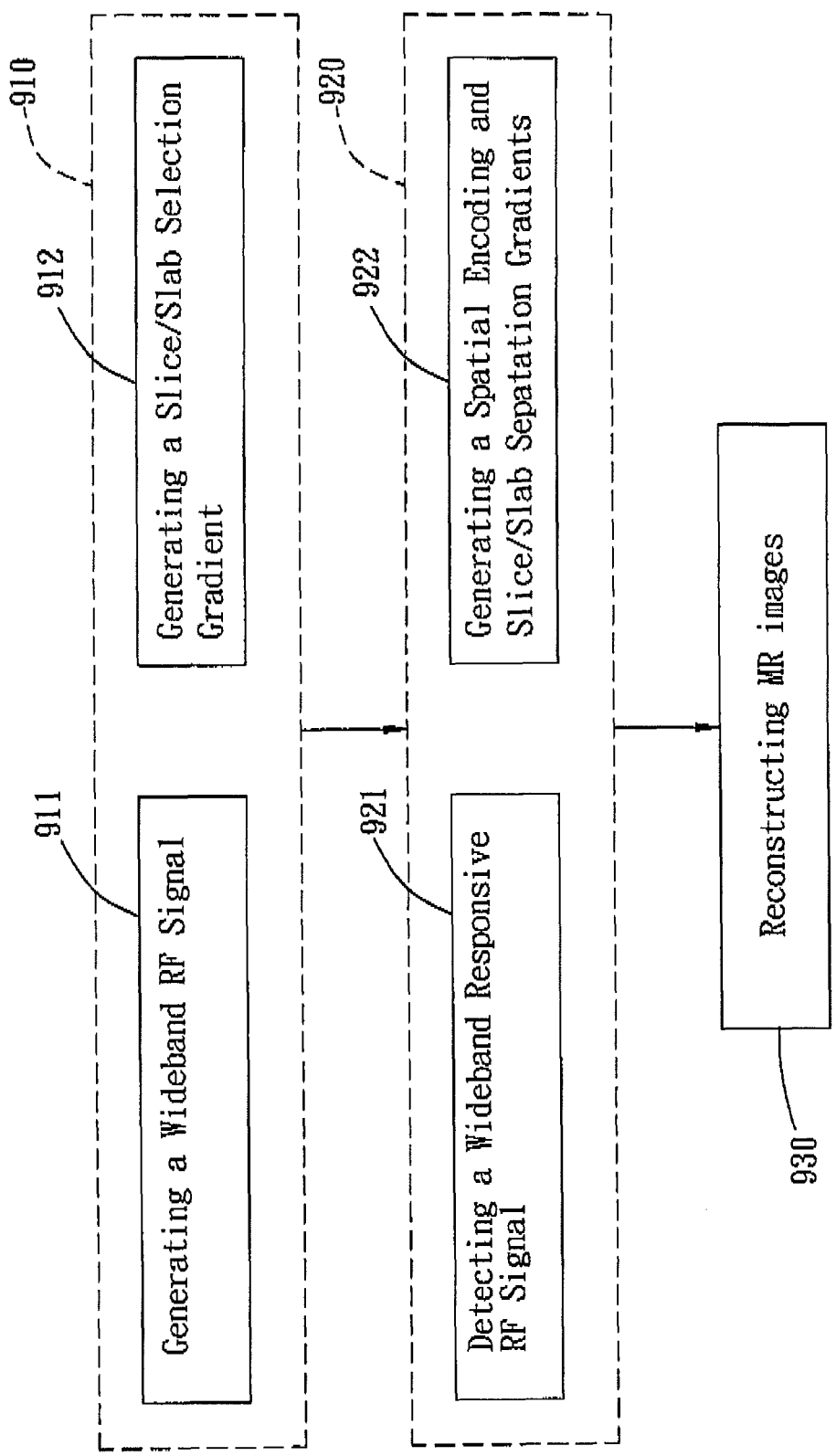
FIG. 9 is a flow chart of an MRI method in accordance with one embodiment.

FIG. 9 is a flow chart of an MRI method in accordance with one embodiment. In operation 910, which is an excitation operation, a wideband RF signal is generated (in sub-operation 911), having a plurality of frequency bands respectively corresponding to a plurality of different kinds of nuclei. Additionally, a slice/slab selection gradient $G_{ss}$, slice for 2D and slab for 3D, to the measurement space is simultaneously generated (in sub-operation 912).

In operation 920, which is a reception operation, a wideband responsive RF signal generated by the different kinds of nuclei is detected (in sub-operation 921), having a plurality of frequency bands that are respectively emitted by the different kinds of nuclei when relaxing from excitation states to lower energy states. Additionally, a spatial encoding gradient $G_{enc}$ and a slice/slab separation gradient $G_{sep}$, slice for 2D and slab for 3D, are also generated to add spatial information to the responsive RF signal (in sub-operation 921). In preferable embodiments, the spatial encoding gradient $G_{enc}$ comprises a gradient $G_{spen}$ generated simultaneously with the slice/slab separation gradient $G_{sep}$ when the wideband responsive RF signal is detected.

In operation 930, which is an image reconstruction operation, MR images for the different kinds of nuclei are reconstructed according to the detected responsive RF signal acquired in operation 921.

It should be noted that, with the provision of the slice/slab separation gradient $G_{sep}$ in the reception procedure, two neighboring frequency components in each frequency band in the FID signal can be separated to a desired degree. However, the slice/slab separation gradient $G_{sep}$ may disadvantageously cause unwanted blur in reconstructed MR images, thus deteriorating the image quality of the reconstructed MR images. The image blur may be along the encoding direction of the spatial encoding gradient $G_{spen}$. Appropriate determination for some related physical quantities in the wideband MRI apparatus 200 can be performed so that that the image blur can be remedied to meet practical needs.

Figure 10:
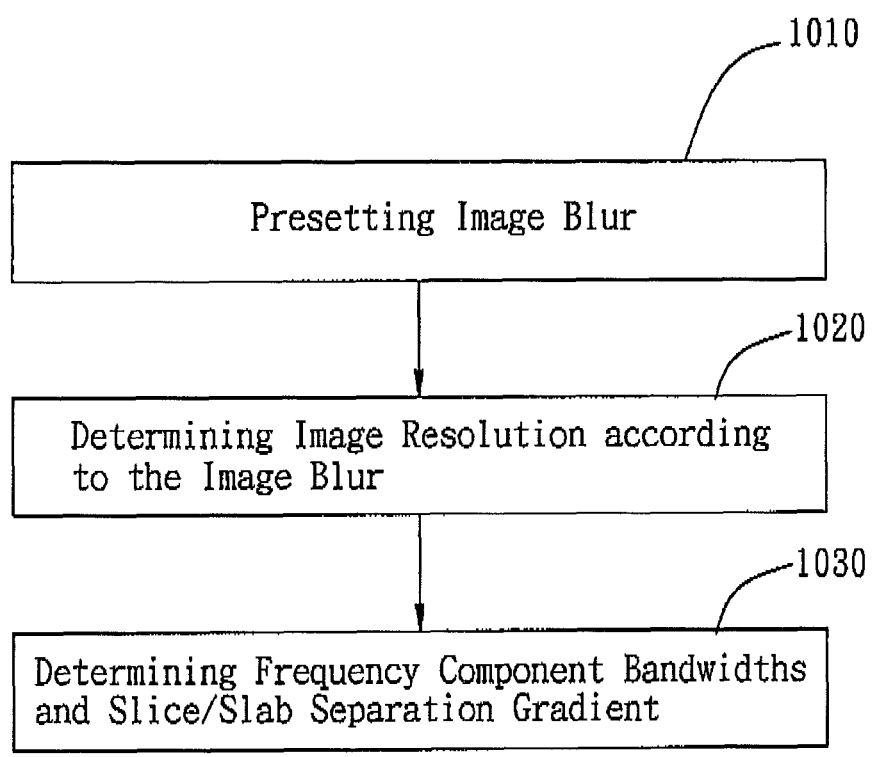
FIG. 10 is a flowchart of MR image quality optimization in accordance with one embodiment.

FIG. 10 is a flowchart of MR image quality optimization in accordance with one embodiment, illustrating operations of determination of several physical quantities in the wideband MRI apparatus 200 in FIG. 2 or the MRI method of FIG. 9.

In operation 1010, the image blur for each kind of nucleus $NUC_i$ (i in an integer and i=1~n) is preset, e.g., in a desired range. The image blur can be an adjustable parameter determined by a user according to practical needs for an acceptable degree of image quality. In accordance with one embodiment, very good, good, and poor image quality can be acquired respectively when blur (pixel)<1, 1≤blur (pixel)<3, and 3≤blur (pixel). In some other embodiments, this operation may be performed according to other various needs that have different requirements for image blur.

In operation 1020, the image resolution along the normal direction, e.g., along the z-axis, of the respective excited slice(s)/slab(s) for each kind of nucleus $NUC_i$ is determined according to the corresponding image blur preset in operation 1010. In one embodiment with a time-invariant linear slice/slab separation gradient $G_{sep}$, the respective image blur for the nucleus $NUC_i$ can be expressed as:

$$blur_i(\text{in mm}) = res_{normal,i} \times G_{sep}/G_{spen}, \quad (Eq. 4.1)$$

$$blur_i(\text{in pixels}) = blur_i(\text{in mm})/res_{spen,i}, \quad (Eq. 4.2)$$

In these equations, $blur_i$ denotes the degree of the image blur for nucleus $NUC_i$. Additionally, $res_{normal,i}$ denotes the image resolution along the normal direction (e.g. along the z-axis) of the excited slice(s)/slab(s) for nucleus $NUC_i$. Specifically, in 2D cases, the image resolution $res_{normal,i}$ along the normal direction, e.g., along the z-axis, of the excited slice(s) is the thickness of one slice along the normal direction, e.g., along the z-axis, of the slice(s). In 3D cases, the image resolution $res_{normal,i}$ along the normal direction, e.g. along the z-axis, of the excited slab (s) is the ratio of the thickness of one slab along the normal direction, e.g. along the z-axis, along the slab to the number of the spatial encoding along the normal direction along the slab. Additionally, $G_{sep}$ denotes the intensity of the slice/slab selection gradient $G_{ss}$, which may be along the z direction and in Gauss/centimeters. Additionally, $G_{spen}$ denotes the intensity of the spatial encoding gradient $G_{spen}$, e.g., in Gauss/centimeter, which may be the intensity of $G_x+G_y$, $G_x$, or $G_y$, depending on the generation sequences of the gradients. Additionally, $res_{spen,i}$ denotes the resolution along the direction of the spatial encoding gradient $G_{spen}$ for nucleus $NUC_i$.

Combining Eqs. 3, 4.1 and 4.2, the image resolution $res_{normal,i}$ for nucleus $NUC_i$ can therefore be determined according to the preset image blur $blur_i$ (in pixels) as the following equation:

$$res_{normal,i} = [blur_i(\text{in pixel}) \times d_{sep,i} \times res_{spen,i}]/FOV_{spen}, \quad (Eq. 5)$$

where the image blur $blur_i$ (in pixels) has been determined in operation 1010. Additionally, the absolute distance $d_{sep,i}$ between two neighboring slices/slabs for nucleus $NUC_i$, and the resolution $res_{spen,i}$ and the field of view $FOV_{spen}$ along the direction of the spatial encoding gradient $G_{spen}$, for example, can all be adjustable parameters set according to practical need.

In operation 1030, bandwidths of the respective frequency components within frequency band $B_i$ and the intensity of the slice/slab selection gradient $G_{ss}$ are determined according to the image resolution $res_{normal,i}$ determined in operation 1020.

Figure 11:
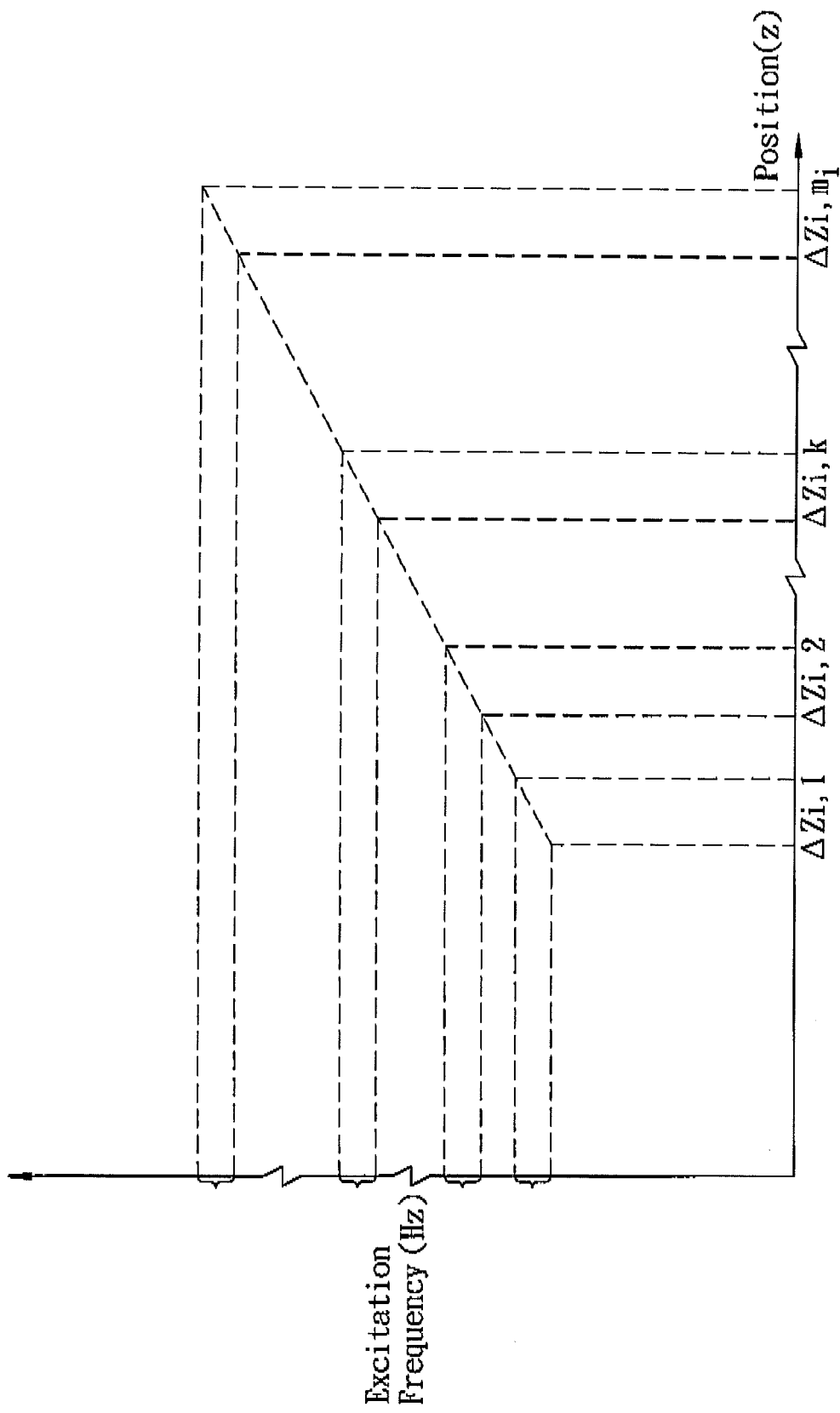
FIG. 11 is an exemplary diagram illustrating the relationship between the bandwidths of frequency components and the thicknesses of corresponding slices/slabs in accordance with one embodiment.

FIG. 11 is an exemplary diagram illustrating the relationship between the bandwidths of frequency components in a single frequency band of the RF signal and the thicknesses of corresponding slices/slabs for the embodiment shown in FIG. 7A or 7B. As shown, each frequency component fi, k (i and j are integers and i=1~n, and k=1~$m_i$) has a respective narrow bandwidth Δfi,k, which excites a slice/slab Si, k having a thickness Δzi,k that can be expressed as:

$$\Delta z_{i,k} = \Delta f_{i,k}/(G_{ss} \times \gamma_i) \quad (Eq. 6).$$

Accordingly, the respective bandwidth Δfi, k of each frequency component fi, k within the band $B_i$ of the RF signal and the intensity $G_{ss}$ of the slice/slab selection gradient $G_{ss}$ can be determined according to Eq. 6, where the thickness Δzi, k has been determined along with the image resolution $res_{normal,i}$ in operation 1020.

According to Eqs. 5 and 6, the image blur is proportional to the product of slice/slab thickness, frequency component bandwidth, and the intensity $G_{ss}$ of the slice/slab selection gradient $G_{ss}$. Accordingly, the image blur of the reconstructed images for the nucleus $NUC_i$ can be effectively reduced by decreasing the bandwidths of frequency components within the corresponding frequency band $B_i$ and/or by increasing the intensity $G_{ss}$ of the slice/slab selection gradient $G_{ss}$.

In summary, the abovementioned embodiments pioneer to simultaneously excite/acquire slices/slabs for different kinds of nuclei at the same or different locations, thus saving considerable total imaging operation time. Specifically, for conventional technologies, excessive time is required to spend on sequentially exciting and acquiring the slices/slabs S 1, 1, S 1, 2, ..., S 1, $m_1$, S 2, 1, S 2, 2, ..., S 2, $m_2$, ... Sn, 1, Sn, 2, ..., and Sn,$m_n$, so in total, N=($m_1+m_2+...+m_n$) times of imaging operations are performed. In the abovementioned embodiments, however, only a one-time imaging operation is required to simultaneously excite and acquire all N slices/slabs, so the total number is merely 1/N that of the conventional technology. Consequently, numerous advantages and benefits can be brought about. For example, for clinical applications, diagnosis time can be significantly shortened, thus enhancing the efficiency of medical service and reducing the suffering or tension of patients. This considerable time saving is also always highly appreciated in other applications.

Additionally, the ability to simultaneously acquire MR images for different embodiments also solves the problem occurring in conventional technologies that MR images for different nuclei cannot be captured one time and real physiological activities within a subject cannot be faithfully demonstrated due to sequential MR imaging operations. The acquired MR images for different kinds of nuclei reveal different kinds of information about the scanned object, for example, different physiological activity information, different disease information, in different parts of a living body. Accordingly, the embodiments can achieve more accurate, complete and profound observation on a scanned subject. For clinical applications, for example, the precision of the diagnosis and the effectiveness of disease tracking can therefore be tremendously increased.

Moreover, the effect of the slice/slab separation gradient on image blur is provided in the above-mentioned embodiments, enabling image quality optimization to be realized by appropriately setting related physical quantities, which can include reducing image blur by decreasing the bandwidths of frequency components within the frequency band and/or by increasing the intensity of the slice/slab selection gradient.

Furthermore, the embodiments can be employed to accomplish whole-subject, e.g., whole-body, scanning. Such whole-body scanning saves considerable MR imaging time, particularly for large area imaging and/or different kinds of nuclei scanning.

In some embodiments realizing whole-subject, e.g., whole-body, scanning, the coil element(s) in the RF excitation module 232 and the RF receiving module 234 can be implemented to cover the whole subject, e.g., the whole body, such that slices/slabs for different kinds of nuclei within the whole body can be simultaneously excited and detected. Accordingly, MR images for different kinds of nuclei within the whole body are allowed to be simultaneously acquired. In such embodiments, technologies achieving higher homogeneity for a static magnetic field in large area, i.e., the coverage area for the whole body, are preferably employed, for the benefit of improving MR image qualities.

In some other examples, as an alternative, a sliding bed/table can be implemented in a measurement space to carry a subject and slide with time during an imaging operation. The coil element(s) in RF excitation module 232 and RF receiving module 234 can then be implemented to cover merely a part of the subject, e.g., a living body, such that slices/slabs for different kinds of nuclei within the part can be simultaneously excited and detected. Sliding movement of the sliding bed/table over time permits different parts of the subject lying on the sliding bed/table to be excited and detected sequentially. By collecting the data acquired from different parts of the body, MR images for different kinds of nuclei within the whole body can still be acquired. Compared with the whole-body coverage embodiments, because the excited and detected area, i.e., the coverage area for part of the body, in such embodiments can be smaller, the embodiments can be realized without requiring high homogeneity of the static magnetic field in a large area.

In an embodiment, the wideband MRI apparatus 200 may be used to perform diffusion imaging. Some examples of diffusion imaging may be Diffusion Weighted Imaging (DWI), Diffusion Tensor Imaging (DTI), Diffusion Spectrum Imaging (DSI), HARDI, and Q-ball. Diffusion imaging may provide in vivo microscopic information of intrvoxel fiber orientation by probing the diffusion of water molecules. In diffusion weighted imaging, a type of diffusion imaging, $T_2$-weighted images may show contrast produced by measuring a loss of coherence or synchrony between water protons. This can generate contrast between an area of pathology and surrounding healthy tissue. In diffusion tensor imaging, another type of diffusion imaging, anisotropic diffusion may be measured to determine the orientation of structures. For example, the structures may be fiber tracts in tissues or nerve fiber tracts within brain white matter.

FIG. 12 is a process flow illustrating a diffusion imaging sequence for simultaneous diffusion imaging of multiple cross sections, such as slices or slabs, according to an embodiment. The process flow of FIG. 12 may apply to either of FIG. 13 or 14.

Figure 13:
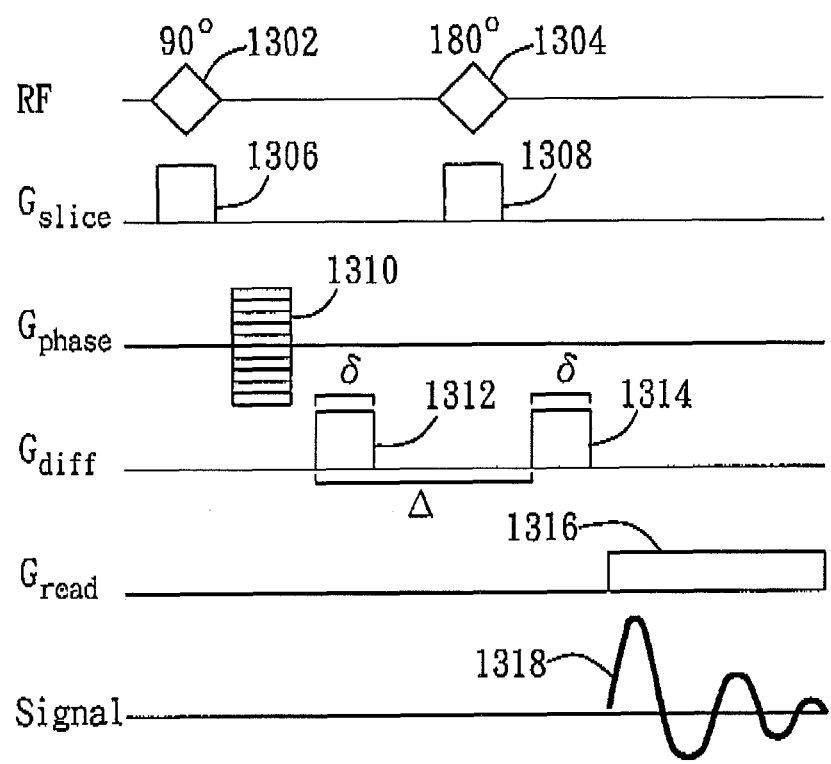
FIG. 13 is a timing diagram of simultaneous diffusion imaging of multiple cross sections using a gradient echo in accordance with one embodiment.

Referring to FIGS. 13 and 14 as well as FIG. 12, in operation 1210, a plurality of data collection sequences are performed. Each data collection sequence includes application of an excitation radio frequency signal 1302, 1402 and a selection gradient 1306, 1406. The excitation radio frequency signal 1302, 1402 may be generated by the RF excitation module 232 in the RF system 230 in response to the sequence controller 210.

The excitation radio frequency signal 1302, 1402 includes a first set of frequency bands selected to simultaneously excite a first nuclei type in a plurality of cross sections of the subject. For example, the first set of frequency bands may include the plurality of frequency bands $B_1$ of FIG. 3 that correspond to a nuclei $NUC_1$, and the plurality of cross sections may include the slices/slabs 380A of FIG. 3. The excitation radio frequency signal 1302, 1402 may also include a second set of frequency bands selected to simultaneously excite a plurality of additional nuclei types in the plurality of cross sections of a subject. For example, the second set of frequency bands may include the plurality of frequency bands $B_2$ through $B_n$ of FIG. 3 that correspond to nuclei $NUC_2$ through $NUC_n$, and the plurality of cross sections of the subject may further include slices/slabs 380B through 380N. Each frequency band of the first and second set of frequency bands may correspond to a particular slice/slab 580A that is separate from the other slice/slabs 580A along the Z-axis, as shown in FIG. 5A. Alternatively, multiple frequency bands from the first and second set of frequency bands (e.g., $B_i$ and $B_j$) may correspond to overlapping slice/slabs 580B, as shown in FIG. 5B.

Formation of the magnetic resonance signal 1318, 1418 occurs after application of the excitation radio frequency signal 1302, 1402, and may be caused by a spin echo method or a gradient echo method, as illustrated respectively in FIGS. 13 and 14. If the gradient echo method is used, each data collection sequence further includes switching the spatial encoding gradient 1410 to generate the magnetic resonance signal 1418 after application of the excitation radio frequency signal 1402. If the spin echo method is used, a refocusing radio frequency signal 1304 is applied to generate the magnetic resonance signal after application of the excitation radio frequency signal 1302. The refocusing radio frequency signal 1304 may include the first set of frequency bands selected to simultaneously excite the first nuclei type in the plurality of cross sections of the subject. The refocusing radio frequency signal 1304 may further include the second set of frequency bands to simultaneously refocus the plurality of additional nuclei types disposed in the plurality of additional cross sections of the subject. A selection gradient 1308 may be applied with the refocusing radio frequency signal 1304.

Each data collection sequence of operation 1210 includes application of a spatial encoding gradient 1310, 1410 during formation of the magnetic resonance signal 1318, 1418. The spatial encoding gradient 1310, 1410 may include a phase-encoding gradient and a frequency-encoding gradient. The spatial encoding gradient 1310, 1410 may be applied after formation of the magnetic resonance signal 1318, 1418. The spatial encoding gradient 1310, 1410 may be generated by a single gradient coil 244 or a plurality of gradient coils 244.

Each data collection sequence of operation 1210 further includes application of a diffusion gradient 1312, 1412 during formation of the magnetic resonance signal 1318, 1418. For the spin echo method of FIG. 13, a pair of diffusion gradients 1312, 1314 that are each applied for a duration δ. Each pair of diffusion gradients 1312, 1314 of the spin echo method may be separated by a duration Δ, with the first diffusion gradient 1312 occurring before the refocusing radio frequency signal 1304 and the additional diffusion gradient 1314 occurring after the refocusing radio frequency signal 1304. The effects of the diffusion gradient on stationary spins may be cancelled out, while spins that have moved during the duration δ may acquire a change in phase. For the gradient echo method of FIG. 14, each data collection sequence of operation 1210 may include a single diffusion gradient 1412.

Each data collection sequence of operation 1210 further includes, during acquisition of the magnetic resonance signal 1318, 1418, application of a separation gradient 1316, 1416 to change a frequency separation between portions of the magnetic resonance signal 1318, 1418; For example, as shown in FIG. 8, neighboring or overlapping frequency components in a frequency band $B_i$ (i=1 to n) of the magnetic resonance signal 1318, 1418 may be separated when the intensity of an applied separation gradient 1316, 1416 is increased. A single gradient coil 244 or a plurality of gradient coils 244 may be used to generate the separation gradient 1316, 1416. A single receiving radio frequency coil or a plurality of receiving radio frequency coils (not illustrated) of the RF receiving module 234 may be used to acquire the respective magnetic resonance signal 1318, 1418 of each data collection sequence.

In an embodiment, each cross section may be scanned with multiple differently oriented diffusion gradients to determine which directions diffusion may be occurring within each cross section. Greater diffusion in a particular direction may correspond to surrounding structure that permits diffusion along a particular direction but restricts diffusion in other directions. For example, alignment of neural fibers may correspond to increased diffusion along a direction.

In operation 1220, a diffusion image of each of the plurality of cross sections is computationally determined as a function of a data set of each of the plurality of data collection sequences and a gyromagnetic ratio of the first nuclei type. Each data set may include a respective magnetic resonance signal 1318, 1418, a respective separation gradient 1316, 1416, and a respective diffusion gradient 1312, 1412. In embodiments in which the spin echo method is applied, each data set may further include a respective additional diffusion gradient 1314. The diffusion image may be computationally determined by the image processing module 256 before being displayed using the display device 260.

To obtain the diffusion image computationally, the effective diffusion $D_{\it eff}$ may be determined from the following equations. The applied magnetic field gradient may be:

$$G(t) = (G_x(t), G_y(t), G_z(t))^T \quad \text{(Eq. 7)}$$

and $$\int_0^t F(t'')ty''; f = F\left(\frac{TE}{2}\right) \quad \text{(Eq. 8)}$$

The effective diffusivity and the logarithm of the echo intensity may be related according to:

$$\ln\left[\frac{A(TE)}{A(0)}\right] = -bD_{\it eff} \quad \text{(Eq. 9)}$$

where $$b = \gamma^2 \int_0^{TE} \left(F(t') - 2H\left(t' - \frac{TE}{2}\right)f\right)^T \left(F(t') - 2H\left(t' \frac{TE}{2}\right)f\right) dt' \quad \text{(Eq. 10)}$$

and where A(TE) is the magnitude of the magnetization at the time of the echo, γ is the gyromagnetic ratio of a nuclei, A(0) is the initial transverse magnetization (at t=0$^+$)), and H(T) is the unit Heaviside function.

$D_{\it eff}$ may have three orthogonal eigenvectors, $\epsilon_1$, $\epsilon_2$, and $\epsilon_3$ and three eigenvalues $\lambda_1$, $\lambda_2$, and $\lambda_3$:

$$D_{\it eff}\epsilon_i = \lambda_i \epsilon_i \text{ for } i=\{1,2,3\}. \quad \text{(Eq. 11)}$$

In an embodiment, when performing diffusion tract imaging, the eigenvector associated with the largest eigenvalue may correspond to a tissue's fiber-tract axis, while the two remaining eigenvectors perpendicular to it define the two remaining orthotropic axes.

FIG. 15A illustrates how a conventional diffusion imaging process of a subject may take approximately 16 seconds to sequentially acquire images of each cross section. FIG. 15B illustrates how in one embodiment, a plurality of diffusion images may be acquired simultaneously from two cross sections at a time to reduce the total scan time.

FIG. 16A illustrates a pair of cross sections from which diffusion images are simultaneously acquired according to one embodiment. FIG. 16B illustrates the pair of diffusion images acquired simultaneously that correspond to the cross sections of FIG. 16A.

FIG. 17 illustrates a diffusion image composed of a first eigenvector map of one of a plurality of cross sections of a subject from which diffusion images were simultaneously acquired, according to one embodiment. The diffusion image illustrates radiating patterns that correspond to anatomical structure of the subject.

While certain embodiments have been described above, the embodiments described are presented only as examples, and this invention is intended to cover various arrangements included within the spirit and scope of the broadest interpretation to encompass all such modifications and equivalent arrangements.

What is claimed is:

1. A diffusion imaging method, comprising:
   performing a plurality of data collection sequences, wherein each data collection sequence includes
      applying an excitation radio frequency signal and a selection gradient, the excitation radio frequency signal including a first set of frequency bands selected to simultaneously excite a first nuclei type in a plurality of cross sections of a subject,
      applying a diffusion gradient during formation of a magnetic resonance signal,
      applying a spatial encoding gradient during formation of the magnetic resonance signal, and
      while acquiring the magnetic resonance signal, applying a separation gradient to change a frequency separation between portions of the magnetic resonance signal; and
   computationally determining a diffusion image of each of the plurality of cross sections as a function of a data set of each of the plurality of data collection sequences and a gyromagnetic ratio of the first nuclei type, each data set including a respective magnetic resonance signal, a respective separation gradient, and a respective diffusion gradient.

2. The diffusion imaging method of claim 1, wherein each data collection sequence further includes
   applying a spatial encoding gradient after formation of the magnetic resonance signal, the spatial encoding gradient comprising a phase-encoding gradient and a frequency-encoding gradient.

3. The diffusion imaging method of claim 1, wherein the plurality of cross sections are all slices or all slabs.

4. The diffusion imaging method of claim 1, wherein each magnetic resonance signal is caused by a spin echo method or a gradient echo method.

5. The diffusion imaging method of claim 1, wherein each data collection sequence further includes switching the spatial encoding gradient to generate the magnetic resonance signal using a gradient echo method.

6. The diffusion imaging method of claim 1, wherein each data collection sequence further includes applying a refocusing radio frequency signal to generate the magnetic resonance signal using a spin echo method after application of the excitation radio frequency signal.

7. The diffusion imaging method of claim 6, wherein
   the excitation radio frequency signal includes a second set of frequency bands selected to simultaneously excite a plurality of additional nuclei types in the plurality of cross sections of a subject, and
   the refocusing radio frequency signal includes the second set of frequency bands to simultaneously refocus the plurality of additional nuclei types disposed in the plurality of additional cross sections of the subject.

8. The diffusion imaging method of claim 1, wherein a gradient coil is used to generate the separation gradient, and a receiving radio frequency coil is used to acquire the respective magnetic resonance signal of each data collection sequence.

* * * * *